United States Patent
Kasano

[11] Patent Number: 5,817,139
[45] Date of Patent: Oct. 6, 1998

[54] SKIN-CONTACT TYPE ANTIALLERGIC SKIN-THERAPEUTIC APPARATUS USING VOLTAGE PULSE TRAIN

[75] Inventor: Hiroyuki Kasano, Kanazawa, Japan

[73] Assignee: Polytronics, Ltd., Ishikawa-ken, Japan

[21] Appl. No.: 861,867

[22] Filed: May 22, 1997

[51] Int. Cl.$^6$ ................................................. A61N 1/30
[52] U.S. Cl. ............................................................ 607/72
[58] Field of Search ........................... 607/50, 72, 115, 607/145, 147, 150

[56] References Cited

U.S. PATENT DOCUMENTS

| | | | |
|---|---|---|---|
| 642,849 | 2/1900 | Otto | 607/147 |
| 1,532,463 | 4/1925 | Winterfield | 607/147 |
| 4,895,154 | 1/1990 | Bartelt et al. | |
| 5,058,605 | 10/1991 | Slovak | 607/72 |
| 5,273,033 | 12/1993 | Hoffman | 607/72 |

FOREIGN PATENT DOCUMENTS

0 289 572   1/1916   Germany ................................ 607/115

*Primary Examiner*—William E. Kamm
*Attorney, Agent, or Firm*—Frishauf, Holtz, Goodman, Langer & Chick

[57] ABSTRACT

A skin-contact type therapeutic apparatus has a pair of electrodes which are put in contact with skin at different areas at the same time and a voltage pulse train generator circuit connected to the pair of electrodes. The voltage pulse generator circuit generates a unipolar voltage pulse train having a pulse width of 100 $\mu$s to 10 ms, a duty ratio of 50% or smaller, a frequency of 20 to 800 Hz, and a peak voltage of 0.05 to 20 V. By pressing the pair of electrodes against skin and applying such a unipolar voltage pulse train, it is possible to treat the skin to resolve allergic dermatitides and/or enhance metabolism by suppressing allergic reactions, and to regenerate skin in a short time without using medicine.

9 Claims, 4 Drawing Sheets

SKIN-CONTACT TYPE ANTIALLERGIC SKIN-THERAPEUTIC APPARATUS USING VOLTAGE PULSE TRAIN

This application is based upon Japanese Patent Application Hei 6-273364 filed on Nov. 8, 1994, the entire contents of which are incorporated herein by reference.

BACKGROUND OF THE INVENTION

1. Field of the Invention

The present invention relates to a skin-contact type therapeutic apparatus for remedying skin damages and/or enhancing metabolism by suppressing allergic reactions of skin.

2. Description of the Related Art

There are many types of allergic reactions of skin in daily life. Allergic reaction occurs when an allergen invades body and the immune system reacts therewith. Allergic dermatitides are mainly classified into exogenous inflammation caused, for example, by insect bite and endogenous inflammation caused, for example, by an allergen of digested food. Although the mechanism of allergic dermatitides is not still elucidated, it is said that imflammation, particularly endogenous imflammation, reflects the present day environment. It is also said that pollinosis, atopic dermatitis, and the like are caused not by a single allergen but by complex contamination of food, air, and water. Of allergic dermatitides, causes of exogenous inflammation can be easily identified and this inflammation is relatively easy to cure. For example, an insect bite causes allergic reactions because of permeated insect saliva and toxicant. This inflammation is easy to treat because the allergen causing eruption and itch is localized near the skin surface at the initial stage. However, if no treatment is made, the inflammation may become serious as the allergen diffuses through bloodstream deep into the body, making it difficult to cure. Insects which attack frequently in daily life include mosquitoes, fleas, acarids, bees, moths, and the like. General treatment for allergic reactions to such insects is to take, inject, or coat an antiallergic medicine such as adrenaline, ephedrine, and antihistamine. For the toxic liquid of an insect, an alkali solution such as diluted ammonium solution is coated to neutralize acid components of the toxic liquid.

For endogenous disease such as atopic dermatitis, there are not so many efficacious medicines except steroid hormones, and if the allergen is not identified, treatment is difficult. The reason for this may be ascribed to the fact that Langerhans' cells in skin having antigen-presenting action are activated abnormally and produce sensitive reactions with other stimuli. It is therefore necessary for treatment of endogenous disease to eliminate the allergen and give medicine, and at the same time to continue daily life with less stimuli.

As described above, allergic dermatitis, irrespective of whether it is acute or chronic, may be accompanied by eruption, itch, or pain. If allergic dermatitis becomes serious, it is accompanied by purulence, muscular pain, or neuralgia, and at worst the patient may die from shock. For treatment, in addition to elimination of allergen, it is necessary to use medicines having a strong effect such as antiallergic medicine and adrenocortical hormones. If treatment timing is delayed, disease may progress for a long time until it is cured. Problems therefore occur with respect to side effects and efficacy and with respect to the patient continuing a normal daily life.

SUMMARY OF THE INVENTION

It is an object of the present invention to provide a skin-contact type therapeutic apparatus which is simple in structure and easy to use, and which is capable of efficaciously calming skin allergic reactions while reducing required amounts of medicine as much as possible.

It is another object of the present invention to provide a skin-contact type therapeutic apparatus which is simple in structure and easy to use, and which is capable of remedying skin damage quickly without depending upon a dose of medicine.

According to one aspect of the present invention, there is provided a skin-contact type therapeutic apparatus comprising: a pair of electrodes put in contact with skin at different areas at the same time; and a voltage pulse train generator circuit for applying a unipolar voltage pulse train between the pair of electrodes, the unipolar voltage pulse train having a pulse width of 100 $\mu$s to 10 ms, a duty ratio of 50% or smaller, a frequency of 20 to 800 Hz, and a peak voltage of 0.05 to 20 V.

As the pair of electrodes is put in contact with a skin surface and the voltage pulse train generator circuit is drived, the voltage pulse train is applied to the skin. This voltage pulse train application suppresses allergic reactions and shock of skin to be caused mainly by exogeneous inflammation. Without using medicine, the allergic dermatitides can be resolved and/or skin can be regenerated in short time. Therefore, without side effects of medicines or with considerable reduction of side effects, skin damages can be cured.

DETAILED DESCRIPTION OF THE PREFERRED EMBODIMENTS

Embodiments of the invention will be described.

A first embodiment will be described with reference to FIGS. 1A and 1B and FIG. 2.

A therapeutic apparatus of the first embodiment was used for checking the treatment efficacy of insect bites. FIGS. 1A and 1B are respectively a plan view and a bottom view of the handy type therapeutic apparatus of this embodiment. This handy type therapeutic apparatus comprises a body case 1, a pair of electrodes 2 and 3, a pilot lamp 4, a display 5 for displaying a set time and a remaining time, and a timer 6. The pair of electrodes 2 and 3 has also a function of a start switch or one of them is connected to a start switch.

The body case 1 is made of, for example, plastics and has built-in electronic circuits generating a unipolar voltage pulse train and drive circuits. The pair of electrodes 2 and 3 is mounted on the bottom of the body case 1, being spaced apart from each other. The electrodes 2 and 3 are ordinarily made of metal. The same metal may be used for both the electrodes 2 and 3 or different metals may be used. The skin-contact surfaces of the electrodes 2 and 3 are preferably made of materials resistant to sebum, sweat, and dirt, such as a noble metal including gold. Obviously, these materials are not limitative but only illustrative. When the electrodes 2 and 3 are put in contact with skin and pressed against it, a switch turns on and the timer 6 is activated. The pilot lamp 4 is made of a light emitting diode (LED) and turns on when the electronic circuits generate oscillation pulses, to notify the user of an oscillation state. The display 5 is ordinarily made of a liquid crystal display (LCD) and displays an operation start time preset by the timer 6 and decrements the displayed numbers to indicate the remaining time after the switch was turned on. When the displayed number on the display 5 becomes 0, the oscillation stops.

Figure 1A:
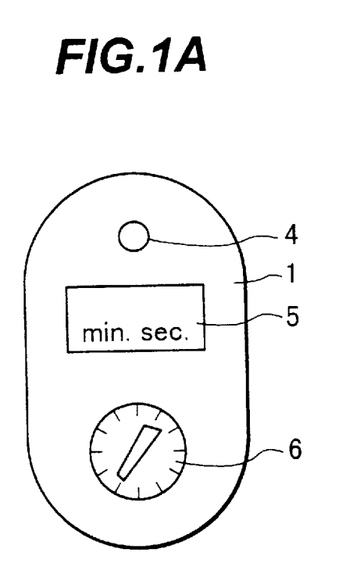
FIGS. 1A and 1B are respectively a plan view and a bottom view of a skin-contact type therapeutic apparatus according to an embodiment of the invention.
Figure 1B:
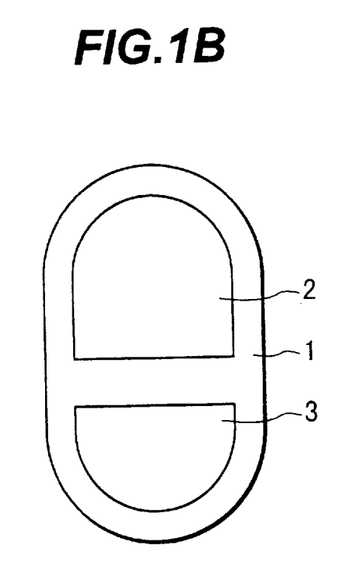
Figure 2:
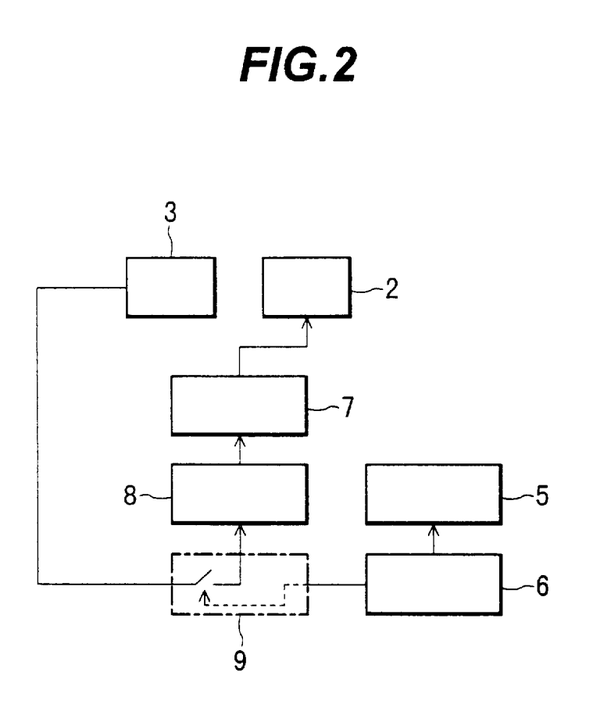
FIG. 2 is a block diagram used for explaining the function of the skin-contact type therapeutic apparatus of the embodiment.

FIG. 2 is a block diagram showing the outline of the circuit structure including electronic circuits built in the body case 1. This apparatus comprises a small voltage pulse oscillator 7, a power source circuit 8, an electronic switch 9, and other elements shown in FIGS. 1A and 1B. The timer 6 outputs an on-signal to the electronic switch 9 during the set time period. The display 5 displays a remaining time which is the set time minus the lapse time. While the timer 6 outputs the on-signal, i.e., during the set time period, the electronic switch 9 turns on. While the switch 9 is on, a voltage (or current) is supplied to the oscillator 7. While this voltage or current is applied, the oscillator 7 outputs a predetermined rectangular wave to the electrode 2. As the electrodes 2 and 3 are put in contact with skin, a closed circuit from oscillator 7, electrode 2, human tissues, electrode 3, electronic switch 9, and oscillator 7 is formed via a through path of power source 8 to apply the rectangular wave to the human tissues. The small voltage pulse oscillator 7 is a compact circuit made of a known transistor oscillator circuit capable of oscillating rectangular waves.

The efficacy of the therapeutic apparatus shown in FIGS. 1A and 1B and FIG. 2 was investigated with patients bit by insects including an Euproctis moth grub, a ctenocephalides felis, and a mosquito. In all cases, initial treatment was performed within one hour after insect bite. Table 1 shows the treatment results. For comparison, the affected parts which are not treated were formed at different skin areas of some patients bit by ctenocephalides felis and mosquito. The rectangular voltage pulse of the therapeutic apparatus shown in FIGS. 1A and 1B and FIG. 2 had a peak voltage of 3 V, a repetition frequency of 250 Hz, a duty ratio of 50%, and a pulse width of 2 ms. A d.c. voltage of the power source circuit was 4.5 V.

TABLE 1

Treatment efficacy of insect bite
Patients: A male 50 yrs, B female 45 yrs, C female 40 yrs, D male 38 yrs Insect: Euproctis moth Patient: A
Diseased part: Left wrist
Treatment frequency, time, period: Two–three times/day, 5 min/treatment, 3 days
Result: Resolution of redness, pain, itch
Insect: *Ctenocephalides felis*

Patient: B
Diseased part: Right leg
Treatment frequency, time, period: Once/day, 1 min/treatment, 1 day
Result: Resolution of redness, itch
Patient: C
Diseased part: Left thigh
Treatment frequency, time, period: Once/day, 1 min/treatment, 1 day TABLE 1-continued Treatment efficacy of insect bite
Patients: A male 50 yrs, B female 45 yrs, C female 40 yrs, D male 38 yrs Result: Resolution of redness, itch
Patient: D
Diseased part: Hypogastrium
Treatment frequency, time, period: Once/day, 3 min/treatment, 1 day
Result: Resolution of redness, itch
Patient: C
Diseased part: Right leg
Treatment frequency, time, period: No treatment for 4 days
Result: Redness 2 cm diameter, swell, itch remained
Patient: D
Diseased part: Right leg
Treatment frequency, time, period: No treatment for 4 days
Result: Redness 1 cm diameter, swell, itch remained
Insect: Mosquito Patient: A
Diseased part: Face
Treatment frequency, time, period: Once/day, 1 min/treatment, immediately
Result: Complete Cure of redness, swell, itch
Patient: A
Diseased part: Right wrist
Treatment frequency, time, period: No treatment for 3 hours
Result: Redness 0.5 cm diameter, itch
Patient: B
Diseased part: Face
Treatment frequency, time, period: Once/day, 1 min/treatment, immediately
Result: Complete Cure of redness, swell, itch
Patient: C
Diseased part: Left foot dorsum
Treatment frequency, time, period: Once/day, 2 min/treatment, immediately
Result: Complete Cure of redness, swell, itch
Patient: C
Diseased part: Right leg
Treatment frequency, time, period: No treatment for 3 hours
Result: Redness, itch remained
Patient: D
Diseased part: Right wrist
Treatment frequency, time, period: Once/day, 2 min/treatment, immediately
Result: Complete Cure of redness, swell, itch The treatment time was preset by the timer 6. After the electrodes 2 and 3 were put in contact with the diseased part, a voltage pulse train was applied during the preset treatment time. The results are shown in Table 1. The treatment did not use medicine and only the physical treatment using this therapeutic apparatus was made.

As seen from Table 1, the treatment efficacy was very good. A brief application of a small voltage pulse train one to three times per day rapidly suppressed allergic reactions of skin inducted by insect bite (saliva or toxic needle) and the inflammation was resolved. The cases where no treatment was made for insect bites by ctenocephalides felis and mosquito showed remaining redness, swell, or itch for several hours to several days. It can therefore be judged that a small voltage pulse train by this therapeutic apparatus achieves efficacious inflammation resolution.

Treatment tests were conducted by changing the oscillation conditions of the small voltage pulse oscillator 7. Treatments were made only for those bites by *Ornithonyssus acarids*. Allergic reaction suppression and inflammation resolution were verified under the conditions in the range of a rectangular pulse width of 100 µs to 10 ms (at a fixed repetition frequency of 100 Hz), a repetition frequency of 50 to 80 Hz (at a fixed pulse width of 500 µs), and a peak voltage of 0.1 to 20 V (at a fixed pulse width of 1 ms and a fixed repetition frequency of 250 Hz).

A number of arborescent Langerhans' cells derived from bone marrow are distributed in an upper side of the stratum basale epidermidis and present transcutaneously invaded allergen to the antibody buildup system. Specifically, as Langerhans' cells capture invaded allergen, reactions of helper T cells are activated to induce strong allergic reactions. At this time, if the unipolar voltage pulse train is applied to the skin surface region where allergen invaded, it can be supposed that Langerhans' cells are temporarily devitalized like under a condition of exposure to strong ultraviolet rays and allergen activates suppressor T cells. This state is immune non-response and suppresses allergic reactions.

The width of a unipolar voltage pulse is required to be 100 µs or more. If the pulse width is smaller than 100 µs, devitalization of Langerhans' cells is insufficient. However, if the pulse width is larger than 10 ms, a problem occurs which is associated with sensing of pulses by Langerhans' cells. Therefore, the pulse width is preferably from 100 µs to 10 ms, and more preferably from 500 µs to 5 ms. If the pulse repetition frequency is 10 Hz or lower, the effect of suppressing allergic reactions cannot be obtained. If the frequency is in the range from 10 to 20 Hz, muscle is subjected to tension/relaxation motion so that myoelectric current becomes noises to lower the effect of suppressing allergic reactions. The duty ratio is preferably 50% or less. If the repetition frequency rises near to 1kHz, voltage pulses are reflected or dispersed during transmission through skin tissues and discrimination between adjacent pulses becomes unclear with respect to Langerhans' cells, so that suppressing allergic reactions become insufficient. The repetition frequency is therefore preferably from 20 to about 800 Hz, and more preferably from 50 to 400 Hz.

In principle, a unipolar voltage pulse having a lower peak value can be used the nearer allergen is localized to the skin surface, i.e., the earlier the treatment is made. Immediately after insect bite, a peak value of only 0.05 V is efficacious. A peak value of about several V is generally applied. If the peak value exceeds 20 V, shock stimuli applied to skin irritated by allergic reactions cause adverse effects. The peak value is therefore preferably from 0.05 V to 20 V and more preferably from 1 to 10 V.

The waveform of a unipolar voltage pulse is ordinarily rectangular. If the above conditions of a pulse voltage are satisfied, the waveform may be a sawtooth waveform (triangular waveform), a sine waveform, or a distorted waveform synthesizing these waveforms. Generally, the pulse voltage is applied for a long time (5 to 10 minutes) if allergic inflammation is heavy, whereas it is applied for a short time (1 to 3 minutes) if the inflammation is light. The effect of suppressing allergic reactions continue for 6 to 24 hours.

A unipolar voltage pulse also influences a number of synapses of peripheral nerve systems distributed in a dermis region. A pulse train applied to presynaptic peripheral nerves causes calcium ions ($Ca^{2+}$) to flow toward the ends of presynaptic peripheral nerves or postsynaptic peripheral nerves, so that synapses are excited. This may be ascribed to an increased sensitivity of receptors of neurotransmitters which is caused by some biochemical reactions of $Ca^{2+}$ and sustained for a considerable time duration. The excitatory postsynaptic potential becomes at a maximum four to five times as high as an ordinary potential. Therefore, skin cells in the region governed by the excited synapses of peripheral nerve systems are physiologically activated and metabolism is enhanced. This hypermetabolism occurs under the similar conditions of a pulse voltage (conditions of suppressing allergic reactions) described above, and continues for several hours to ten and several hours. Physiological activation of synapses cannot be observed definitely if the pulse width and repetition frequency shift away from the above-described range.

A unipolar voltage pulse train under the above-described conditions suppresses allergic reactions and at the same time excites metabolism of cells. As a result, the function of resolving allergic dermatitides and the skin regenerating function can both be induced responsive to insect bites, incised wounds, burns, and the like.

Figure 3:
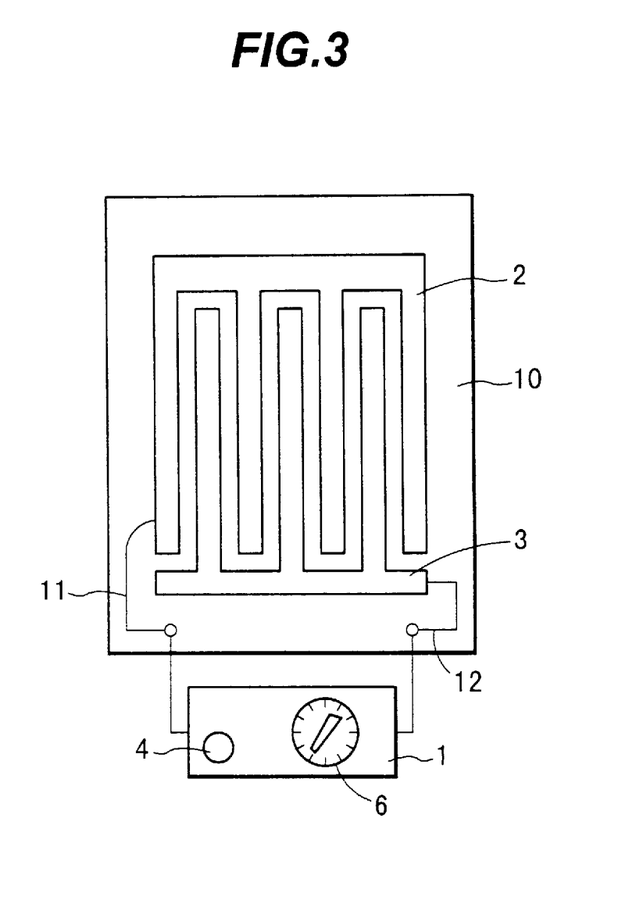
FIG. 3 is a schematic diagram showing the structure of a skin-contact type therapeutic apparatus according to another embodiment.

A second embodiment will be described with reference to FIG. 3. The therapeutic apparatus of the second embodiment is applied to injuries such as wounds and burns in the deep region of skin. FIG. 3 shows a schematic diagram showing the outline of the therapeutic apparatus of the second embodiment.

In this therapeutic apparatus, a pair of electrodes 2 and 3 is made of a metal thin plate plated with gold and has a comb shape. The material of the electrodes 2 and 3 may be a durable material plated with platinum or rhodium or a biocidal material plated with silver. The pair of electrodes 2 and 3 forms flexible electrodes adhered to a thick cloth 10. The electrodes 2 and 3 are connected via conductive wires 11 and 12 to an electronic circuit (not shown) in a body case 1 disposed away from the cloth 10. If removable terminals are connected to the ends of the conductive wires 11 and 12, the electrodes 2 and 3 and cloth 10 can be dumped.

Similar to the first embodiment, a small voltage pulse oscillator, a power source circuit, and an electronic switch such as shown in FIG. 2 are installed in the body case 1. Although a display such as shown in FIG. 2 is not used, it may be used if necessary. A pilot lamp 4 and a timer 6 are mounted so as to allow a user to look at the lamp and access the timer. The timer 6 has a switch function of turning on and off in response to the depression of a button. As the button is depressed after the operation time is set, the small voltage pulse oscillator 7 is driven. The power source circuit is usually a battery. A commercial power supply may be used by providing an adapter and the like, if necessary.

The cloth 10 is tightly attached to skin with a sticking plaster or the like so that the electrodes 2 and 3 are made in contact with a diseased part. The timer 6 is set to a predetermined time and the switch is turned on to apply a small voltage pulse to the injured skin. The therapeutic apparatus was used at a time lapse range within from 10 to 20 minutes after the occurrence of wounds and burns. The treatment results are shown in Table 2.

TABLE 2

Treatment efficacy of wound and burn
Patients: A male 50 yrs, B female 45 yrs, C female 40 yrs, E male 54 yrs, F female 62 yrs, G female 71 yrs, H female 46 yrs Indication: Wound Patient: A
Diseased part: Rear right wrist
Treatment frequency, time, period: Twice/day, TABLE 2-continued Treatment efficacy of wound and burn
Patients: A male 50 yrs, B female 45 yrs, C female 40
yrs, E male 54 yrs, F female 62 yrs, G female 71 yrs, H
female 46 yrs 3 min/treatment, 2 days
Result: Closed wound, swelled new flesh
Patient: B
Diseased part: Left ring finger
Treatment frequency, time, period: Three times/day,
1 min/treatment, 1 day
Result: Closed wound, swelled new flesh
Patient: E
Diseased part: Left leg abrasion
Treatment frequency, time, period: Twice/day,
1 min/treatment, 4 days
Result: Closed wound, pellicle, analgesic
Patient: F
Diseased part: Left ankle bite
Treatment frequency, time, period: Once/day,
5 min/treatment, 2 days
Result: Closed wound, analgesic
Indication: Burn Patient: G
Diseased part: Upper right shoulder
Treatment frequency, time, period: Twice/day,
2 min/treatment, 3 days
Result: Complete cure
Patient: C
Diseased part: Central back
Treatment frequency, time, period: Once/day,
2 min/treatment, 4 days
Result: Complete cure
Patient: H
Diseased part: Right hand dorsum
Treatment frequency, time, period: Twice/day,
3 min/treatment, 4 days
Result: Complete cure After hemostasis, the apparatus was applied to injuries. For the treatment of burns of 2 to 3 degrees (relatively slight degree) with varicellas, the apparatus was applied to an unbleeding diseased part. For all the cases, no medicine was used. The rectangular voltage pulse conditions were a pulse width of 500 $\mu s$, a repetition frequency of 400 Hz, a duty ratio of 30%, and a peak voltage of 8V. The power source voltage was 9V. As seen from the treatment results shown in Table 2, the treatment using this therapeutic apparatus activates metabolism of skin cells and cure wounds while suppressing shock of wounds and burns at peripheral areas and suppressing purulence.

For the comparison purpose, the treatments of other patients with wounds and burns were performed by replacing the small voltage pulse oscillator by a new one and changing the pulse waveform to a triangular waveform and a unipolar sine waveform composed of only the phases of 0 to $\pi$, $2\pi$ to $3\pi$ . . . (both waveforms having a peak voltage of 8 V, a pulse width of 1 ms, and a repetition frequency of 100 Hz). The treatment results were similar to Table 2 and it was confirmed that wounds and burns were cured by an application of a pulse train in a short time without using medicine.

Figure 4:
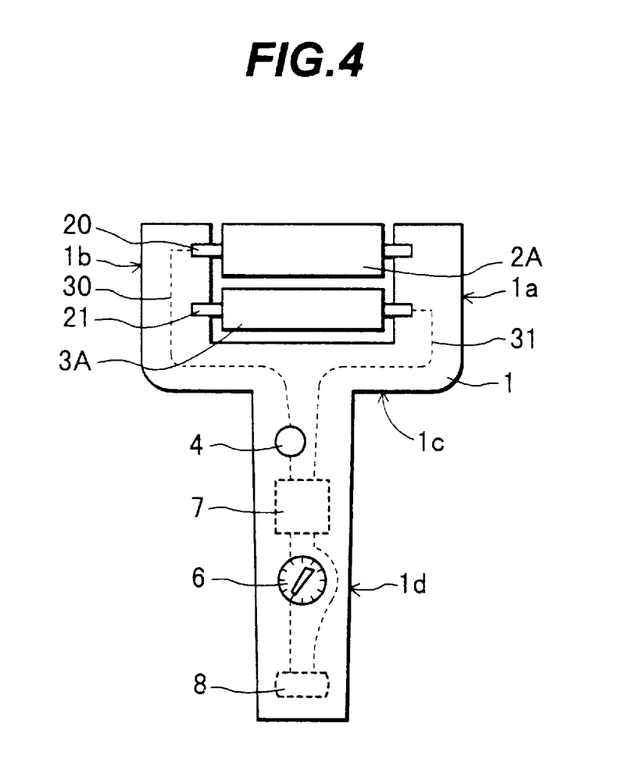
FIG. 4 is a schematic diagram showing the structure of a skin-contact type therapeutic apparatus according to still another embodiment.

A third embodiment of the invention will be described with reference to FIG. 4. The therapeutic apparatus was applied to cornificated skins to check the skin regenerating function. FIG. 4 is a schematic diagram showing the outline of the therapeutic apparatus of the third embodiment. Main parts of the electronic circuits and interconnections in a body case 1 are indicated by broken lines.

The body case 1 of the therapeutic apparatus of the third embodiment is constituted of two arms 1a and 1b disposed in parallel, a coupling portion 1c for coupling the ends of the two arms 1a and 1b, and a grip 1d extending from generally the central area of the coupling portion 1c in the direction opposite to the arms 1a and 1b.

Two rotary shafts 20 and 21 generally in parallel are mounted between the arms 1a and 1b. Cylindrical electrodes 2A and 3A are attached to the rotary shafts 20 and 21. The electrodes 2A and 3A are rotatable around the center axes of the rotary shafts 20 and 21. The surfaces of the electrodes 2A and 3A are plated with platinum.

One end of a lead wire 30 is connected via a slip ring (not shown) to the electrode 2A, and the other end thereof is connected via a pilot lamp 4 to one output terminal of the small voltage pulse oscillator circuit 7. One end of a lead wire 31 is connected via a slip ring (not shown) to the electrode 3A, and the other end thereof is connected via the other output terminal of the pulse oscillator 7. Since the lead wires 30 and 31 are connected via the slip rings to the electrodes 2A and 3A, the conduction state of the lead wires can be retained even during rotation of the electrodes 2A and 3A.

A voltage is applied from the battery power source 8 to the oscillator 7. A timer 6 is inserted into one of two power lines interconnecting the oscillator 7 and battery power source 8. The timer 6 has a switch function.

As the therapeutic apparatus is moved along a skin surface while the electrodes are put in contact with the skin, the electrodes 2A and 3A rotate. The electrodes 2A and 3A may be forcibly rotated by a motor or the like.

After a predetermined time is set by the timer 6, a button of the timer is depressed when the electrodes 2A and 3A simultaneously contact with skin to drive the small pulse voltage oscillator 7 and supply a small voltage pulse train to the electrodes 2A and 3A. At this time, the pilot lamp 4 turns on and the user is notified of the activation of the therapeutic apparatus. If necessary, a display for displaying a remaining time may be used. As the electrodes 2A and 3A are rotated in contact with the skin, a relatively large area of skin can be easily applied with pulse stimuli.

The treatment results of patients with cornificated skins by the therapeutic apparatus shown in FIG. 4 are given in Table 3.

TABLE 3

Treatment efficacy of cornificated layer

Cornificated part: Elbow

Patient: Female 45 yrs
Treatment frequency, time, period: Once/day,
3 min/treatment, 2 days
Result: Complete cure of partial abrasion
(blank-map)
Patient: Male 50 yrs
Treatment frequency, time, period: Once/day,
3 min/treatment, 1 day
Result: Complete cure of stiffness
Patient: Female 33 yrs
Treatment frequency, time, period: Once/day,
2 min/treatment, 1 day
Result: Complete cure of stiffness, flexible
Cornificated part: Malleolus Patient: Female 62 yrs
Treatment frequency, time, period: Once/day,
2 min/treatment, 5 days
Result: flexible, glossy
Patient: Male 54 yrs
Treatment frequency, time, period: Once/day,

TABLE 3-continued

Treatment efficacy of cornificated layer 2 min/treatment, 3 days
Result: flexible, glossy
Cornificated part: Waist Patient: Female 62 yrs
Treatment frequency, time, period: Once/day,
3 min/treatment, 6 days
Result: Complete cure of stiffness
Patient: Male 48 yrs
Treatment frequency, time, period: Once/day,
3 min/treatment, 3 days
Result: Complete cure of stiffness
Cornificated part: Knee Patient: Female 44 yrs
Treatment frequency, time, period: Once/day,
2 min/treatment, 5 days
Result: Complete cure of white-map
Patient: Female 53 yrs
Treatment frequency, time, period: Once/day,
2 min/treatment, 5 days
Result: Complete cure of white-map, glossy The small pulse voltage has a triangular waveform. The pulse conditions were a peak voltage of 6 V, a duty ratio of 25%, a pulse width of 1.4 ms at the 50% pulse peak level, and a repetition frequency of 100 Hz. As seen from Table 3, the treatment results of cornificated skins were also relatively good in short treatment times. This may be ascribed to that synapses of peripheral nerve systems distributed in a skin deep region are physiologically activated and metabolism is enhanced by the small voltage pulse train, while suppressing allergic reactions such as metal allergy. The skin impedances were measured. After the treatment by the therapeutic apparatus, the impedance at the diseased part lowered by about one digit as compared to that before treatment. This phenomenon can be observed often during skin regeneration induced by enhanced synaptic plasticity of nerves. With this embodiment, skin regeneration for cornificated skins is not accompanied by redness, pain, or itch because allergic reactions are suppressed.

The same general regeneration effects were verified by using another therapeutic apparatus of the same type as shown in FIG. 4 in which the oscillation waveform was changed to a unipolar sine waveform and a rectangular waveform and the oscillation conditions were a peak voltage of 6 V, a duty ratio of 25% and a repetition frequency of 100 Hz.

In the above embodiments, the functions of suppressing allergic reactions of skin, remedying skin damages and/or regenerating skin of the therapeutic apparatus of this embodiment have been described. The application of this invention, however, is not limited only to insect bites, wounds, burns, and cornificated layers. For example, the invention is applicable to the growth of scalp hairs on epithelial folliculus pili which is special keratinocyte distributed in a dermis region, and to the suppression and cure of atopic dermatitis which is a kind of endogenous allergy. These applications utilize the complex functions obtained upon application of a unipolar small voltage pulse train satisfying the conditions specific to the invention to diseased skin areas. The complex functions include the temporary formation of local immune non-response, the suppression of allergic reactions and shock, and the activation of metabolism through excitement of synapses of peripheral nerve systems.

The unipolar small voltage pulse is more effective the lighter the degree of skin disease and the shorter the lapse of time from the occurrence of skin diseases, even if the peak voltage and repetition frequency are low. For example, the effect of suppressing allergic reactions was observed even at the peak voltage of about 0.05 V and the repetition frequency of about 20 Hz for the treatment of an insect bite immediately thereafter. However, after allergen diffuses into the deep region after a long time lapse from the occurrence of skin disease, the effect was poor. For example, after the lapse of 12 hours of insect bite, relatively strong stimuli were necessary at the peak voltage of 5 to 20 V of a small voltage pulse and a repetition frequency of 100 to 800 Hz. In both light and serious skin diseases, the width of a small voltage pulse is required to be 100 $\mu$s or larger, and more preferably 500 $\mu$s to several ms.

In the above embodiments, a noble metal is described for use as the electrode material. Although a noble metal is preferable from the viewpoint of durability, general conductive materials may also be used. For example, carbon electrodes and semiconductor electrodes may be used. If one of a pair of electrodes is a noble metal and the other is semiconductor, a chemical cell is formed at the skin-contact surface so that a d.c. electromotive force can be obtained stably. If the pulse voltage described above is applied while ion current generated by a d.c. electromotive force flows subcutaneously, allergen is oxidized and/or reduced by ion current so that the antigen function is weakened. It is therefore possible to suppress allergic reactions by weak pulse stimuli.

The therapeutic apparatus of this invention poses no problem even if it is used with medicine. The shape of the therapeutic apparatus of this invention is not limited to those described above. For example, a pair of electrodes may be woven with a cloth. In summary, it is sufficient if a unipolar small voltage pulse train is used which satisfies the conditions of this invention. Obviously, the pilot lamp and timer are not essential.

The oscillation conditions of a small voltage pulse capable of suppressing allergic reactions of skin have been described in the above embodiments. The pulse oscillation conditions of the therapeutic apparatus are not limited only to those described in the above embodiments. A therapeutic apparatus capable of variably setting the pulse oscillation conditions is intended to fall within the scope of this invention. Such a variable apparatus may be more preferable for the treatment of allergic reactions.

For example, for "skin disease at an early stage" where allergen only permeates to relatively shallow levels, the treatment effects can be expected at a low peak voltage, low repetition frequency, and narrow pulse width. However, it is necessary to apply stronger pulses in order to suppress allergic reactions after a lapse of a long time from the occurrence of skin disease. In many cases, patients and doctors do not always know the pulse conditions most suitable for respective symptoms. It is therefore possible to variably set the pulse oscillation conditions in order to obtain the treatment effects in short time. For example, the small voltage pulse oscillation circuit is provided with an additional circuit which can periodically change the repetition frequency in the range from 50 to 700 Hz while making the peak voltage and pulse width constant. At least ten pulses provide the effect of suppressing allergic reactions. Therefore, even if the repetition frequency changes, the pulses under the optimum conditions and under the nearby conditions can be easily retained by using such an additional circuit.

Instead of changing the repetition frequency, the peak voltage and/or pulse width may be variably set. By adding such a circuit for variably setting the pulse oscillation conditions, the effect of reliably suppressing allergic reactions in short time can be realized.

A dial switch may be mounted on the outside of the body case of the therapeutic apparatus to allow a patient or doctor to set the peak voltage, pulse width and/or repetition frequency as desired. By supplying a proper instruction manual and accumulating experiment data, the pulse oscillation conditions suitable for respective symptoms can be set and treatments in shorter time can be expected. A circuit capable of selectively outputting a rectangular wave, a sine wave, a triangular wave, and the like may be used.

The present invention has been described in connection with the preferred embodiments. However, the invention is not limited only to the above embodiments, and it should be apparent that various modifications, improvements, combinations, and the like can be made by those skilled in the art.

I claim:

1. A skin-contact type therapeutic apparatus for suppressing allergic reactions, comprising:

a pair of electrodes for contacting with skin at different areas at a same time; and a voltage pulse train generator circuit for applying a unipolar voltage pulse train between the pair of electrodes, wherein the unipolar voltage pulse train has a pulse width of 100 $\mu$s to 10 ms, a duty ratio not greater than 50%, a frequency of 20 to 800 Hz, and a peak voltage of 0.05 to 20 V.

2. A skin-contact type therapeutic apparatus according to claim 1, wherein each electrode of the pair of electrodes has a cylindrical skin contact surface, and the apparatus further comprises a support mechanism for respectively supporting each electrode rotatably about a rotation axis.

3. A skin-contact type therapeutic apparatus according to claim 1, wherein the voltage pulse train generator circuit includes means for periodically changing at least one of the pulse width, the frequency, and the peak voltage of the voltage pulse train.

4. A skin-contact type therapeutic apparatus comprising:

a pair of electrodes for contacting with skin at different areas at a same time; and a voltage pulse train generator circuit for applying a unipolar voltage pulse train between the pair of electrodes, wherein the unipolar voltage pulse train has a pulse width of 100 $\mu$s to 10 ms, a duty ratio not greater than 50%, a frequency of 20 to 800 Hz, and a peak voltage of 0.05 to 20 V, and wherein each electrode of the pair of electrodes has a comb shape including teeth, the teeth of one electrode of the pair of electrodes interdigitate with the teeth of the other electrode of the pair of electrodes, and the teeth of the one electrode have tips which point in an opposite direction to the teeth of the other electrode.

5. A skin-contact type therapeutic apparatus comprising:

a pair of electrodes for contacting with skin at different areas at a same time; and a voltage pulse train generator circuit for applying a unipolar voltage pulse train between the pair of electrodes, wherein the unipolar voltage pulse train has a pulse width of 100 $\mu$s to 10 ms, a duty ratio not greater than 50%, a frequency of 20 to 800 Hz, and a peak voltage of 0.05 to 20 V, and wherein each of the pair of electrodes includes a skin-contact surface, and the skin contact surface of one electrode of the pair of electrodes comprises noble metal and the skin-contact surface of the other electrode of the pair of electrodes comprises a semiconductor material.

6. A skin-contact type therapeutic apparatus according to claim 5, wherein each electrode of the pair of electrodes has a comb shape including teeth, and the teeth of one electrode of the pair of electrodes are disposed in mesh mutually with the teeth of the other electrode of the pair of electrodes.

7. A skin-contact type therapeutic apparatus according to claim 5, wherein each electrode of the pair of electrodes includes a cylindrical skin contact surface, and the apparatus further comprises a support mechanism for respectively supporting each electrode rotatably about a rotation axis.

8. A skin-contact type therapeutic apparatus according to claim 5, wherein the voltage pulse train generator circuit includes means for periodically changing at least one of the pulse width, the frequency, and the peak voltage of the voltage pulse train.

9. A skin-contact type therapeutic method for suppressing allergic reactions, comprising the steps of:

pressing a pair of electrodes against skin; and treating the skin by applying a unipolar voltage pulse train between the pair of electrodes, wherein the unipolar voltage pulse train has a pulse width of 100 $\mu$s to 10 ms, a duty ratio not greater than 50%, a frequency of 20 to 800 Hz, and a peak voltage of 0.05 to 20 V.

* * * * *